United States Patent [19]

Beremand et al.

[11] Patent Number: 4,888,282

[45] Date of Patent: Dec. 19, 1989

[54] SYNTHETIC GENE FOR ACYL CARRIER PROTEIN

[75] Inventors: Phillips D. Beremand, Peoria, Ill.; John B. Ohlrogge, Okemos, Mich.; David N. Kuhn, West Lafayette, Ind.

[73] Assignees: The United States of America as represented by the Secretary of Agriculture, Washington, D.C.; Purdue University, W. Lafayette, Ind.

[21] Appl. No.: 58,054

[22] Filed: Jun. 4, 1987

[51] Int. Cl.[4] .................. C12N 9/10; C12N 15/00; C12N 7/00; C12N 1/20

[52] U.S. Cl. ........................... 435/193; 435/172.1; 435/172.3; 435/235; 435/252.33; 435/320; 530/27; 935/14

[58] Field of Search .................. 435/68, 70, 71, 91, 435/172.1, 172.3, 320, 252.3, 193, 252.31–252.35; 536/27; 935/11, 29, 72, 73, 14

[56] References Cited

PUBLICATIONS

Daniel J. Guerra et al., "Purification and Characterization of Recombinant Spinach Acyl Protein I Expressed in *Escherichia coli*", J. Biol. Chem., 263(9): 4386–4391 (Mar. 25, 1988).

Phillip D. Beremand et al., "Synthesis, Cloning, and Expression in *Escherichia coli* of a Spinach Acyl Carrier Protein-I Gene", Arch. Biochem. Biophys., 256(1): 90–600 (Jul. 1987).

T. M. Kuo et al., "The Primary Structure of Spinach Acyl Carrier Protein", Arch. Biochem. Biophys., 234(1): 290–296 (Oct. 1984).

J. B. Ohlrogge et al., "Spinach Acyl-Carrier Proteins: Structure, Regulation, and Progress Towards Cloning", Biochem. Soc. Trans., 14(3): 579–581 (Jun. 1986).

Lathe; J. Mol. Biol., 183:1 (1985).

Amann et al; Gene 40: 183 (1985).

*Primary Examiner*—James Martinell
*Attorney, Agent, or Firm*—M. Howard Silverstein; John D. Fado; Curtis P. Ribando

[57] ABSTRACT

A synthetic gene which encodes for acyl carrier protein (ACP) has been designed. Construction, cloning, and expression in *E. coli* of spinach ACP-I has been demonstrated. In vitro production of ACP by appropriate expression vectors carrying the synthetic gene will augment the meager supply of this protein. Analogous genes designed for expression of ACP in plants would be a useful tool for controlling fatty acid synthesis and metabolism.

9 Claims, 2 Drawing Sheets

A

```
           1   2   3   4   5   6   7   8   9   10  11  12  13  14
      (Met)Ala Lys Lys Glu Thr Ile Asp Lys Val Ser Asp Ile Val Lys

GA TCC ATG GCC AAG AAA GAG ACC ATT GAC AAG GTG TCT GAC ATT GTG AAG
    G TAC CGG TTC TTT CTC TGG TAA CTG TTC CAC AGA CTG TAA CAC TTC 15  16  17  18  19  20  21  22  23  24  25  26  27  28  29  30
   Glu Lys Leu Ala Leu Gly Ala Asp Val Val Val Thr Ala Asp Ser Glu

GAG AAG CTG GCT CTG GGT GCT GAC GTG GTG GTG ACT GCT GAC TCC GAG
   CTC TTC GAC CGA GAC CCA CGA CTG CAC CAC CAC TGC CGA CTG AGG CTC 31  32  33  34  35
   Phe Ser Lys Leu Gly

TTC TCC AAG CTG GGA GCA GCG CGT CG
   AAG AGG TTC GAC CCT CGT CGC GCA GCC TAG
                         Hga I   Bam HI
```

B

```
   Bam HI  Hga I  33  34  35  36  37  38  39  40  41  42  43  44  45
                  Lys Leu Gly Ala Asp Ser Leu Asp Thr Val Glu Ile Val

GA TCC GAC GCC AAG CTG GGA GCT GAT TCC CTT GAC ACT GTG GAA ATT GTG
    G CTG CGG TTC GAC CCT CGA CTA AGG GAA CTG TGA CAC CTT TAA CAC 46  47  48  49  50  51  52  53  54  55  56  57  58  59  60  61
   Met Asn Leu Glu Glu Glu Phe Gly Ile Asn Val Asp Glu Asp Lys Ala

ATG AAC CTT GAG GAG GAG TTC GGC ATC AAT GTG GAT GAG GAC AAG GCT
   TAC TTG GAA CTC CTC CTC AAG CCG TAG TTA CAC CTA CTC CTG TTC CGA 62  63  64  65  66  67  68  69  70  71  72  73  74  75  76  77
   Gln Asp Ile Ser Thr Ile Gln Gln Ala Ala Asp Val Ile Glu Gly Leu

CAA GAC ATC TCC ACC ATC CAA CAA GCT GCT GAT GTG ATT GAG GGC CTC
   GTT CTG TAG AGG TGG TAG GTT GTT CGA CGA CTA CAC TAA CTC CCG GAG 78  79  80  81  82
   Leu Glu Lys Lys Ala

CTT GAA AAG AAG GCC TAA CTC GAG G
   GAA CTT TTC TTC CGG ATT GAG CTC CCT AG
```

Fig-2

SYNTHETIC GENE FOR ACYL CARRIER PROTEIN

BACKGROUND OF THE INVENTION

1. Field of the Invention

In plants, acyl-carrier protein (ACP) exists as a small acidic cofactor protein which participates in at least 12 reactions of fatty acid biosynthesis and metabolism. In recent years, research on this protein has intensified in several laboratories because of the potential of ACP to serve as a representative marker protein for studies of the regulation of plant fatty acid synthetase gene expression. Such studies may eventually have an important practical impact on the selection of genetic engineering strategies used to modify the amount and type of fatty acids produced by oilseed crops. For example, ACP levels have been measured in developing soybean seeds by both enzymic and immunochemical assays [J. B. Ohlrogge et at. I, Plant Physiol. 74: 622–625 (1984)]. A close correlation was found between rates of fatty acid synthesis in vivo and ACP content. These results suggest that levels of fatty acid biosynthetic proteins may be a rate-determining component of the seed's overall lipid biosynthetic capacity. Although other factors such as substrate and cofactor supply may also limit seed oil production, the results with ACP provide encouragement that molecular genetic modification of fatty acid biosynthetic protein levels may provide a means to influence oilseed metabolism.

2. Description of the Prior Art

ACPs have been the first proteins in plant fatty acid biosynthesis to be purified to homogeneity and, to date, the only proteins for which amino acid sequence data are available. Spinach leaf ACP-I has been completely sequenced [T. M. Kuo et al. I, Arch. Biochem. Biophys. 234: 290–296 (1984)], and 72 of 87 residues of the barley leaf ACP-I are known [P. B. Hoj et al., Carlsberg Res. Commun. 48: 284–306 (1983)]. The two plant sequences are 70% homologous, indicating that the ACP structure is highly conserved between monocot and dicot plant species. Comparison with the *Escherichia coli* ACP sequence reveals 40% homology; whereas, the ACP domain of the rabbit multi-enzyme fatty acid synthetase complex has 25% homology with plant or bacterial ACP sequences. These comparisons suggest that all ACPs evolved from a common ancestor, but, intriguingly, the plant structure has remained closer to its bacterial counterpart than to the corresponding animal structure.

Plants have recently been shown to contain multiple isoforms of ACP [P. B. Hoj et al., Carlsberg Res. Commun. 49: 483–492 (1984); J. B. Ohlrogge et al. II, J. Biol. Chem. 260: 8032–8037 (1985)]. Although the isoforms are clearly closely related in structure, there are significant differences in the amino acid composition and the N-terminal sequences of both barley and spinach ACP isoforms. These differences suggest that the isoforms may be coded by multigene families.

The plant ACP isoforms are expressed differently in different tissues (Ohlrogge et al. II, supra). In spinach leaves we find that ACP-I is present at three- to four-fold higher levels than ACP-II. However, in developing spinach seeds ACP-II is the predominant species, with ACP-I absent or barely detectable. Similar results have been observed with castor oil seed leaves and endosperm and soybean leaves and developing cotyledons.

Studies have revealed that ACP is localized essentially exclusively in the plastids of spinach mesophyll cells, but is probably initially synthesized in the cytoplasm. Reported data also suggest that ACP is a nuclear-encoded protein, which is synthesized as a precursor polypeptide containing a transit peptide that guides its uptake by the plastids.

ACPs constitute less than 0.1% of the total cell protein in most species [T. M. Kuo et al. II, Arch. Biochem. Biophys. 230: 110–116 (1984)]. Therefore, purification of milligram quantities is difficult, and, as a consequence, plant lipid biosynthetic studies have been hampered by the absence of adequate supplies of plant ACP for use as cofactor or substrate.

Expression of a plant ACP gene in a suitable vector such as *E. coli* might provide a means of providing sufficient ACP for enzymological and other studies. A synthetic gene encoding only a strutural protein is more likely to produce an active ACP when introduced into *E. coli* than either a genomic clone (with expected intervening sequences, i.e., introns) or a full-length cDNA clone (with an expected transit peptide encoding sequence).

SUMMARY OF THE INVENTION

We have now discovered a strategy for constructing, cloning, and expressing synthetic acyl carrier protein genes. The novel genes contemplated by the invention are designed to have a high level of homology with the naturally occurring ACP genes.

In accordance with this discovery, it is an object of the invention to provide synthetic genes encoding for proteins which are structurally homologous and functionally identical to authentic acyl carrier proteins.

It is also an object of the invention to clone the ACP gene in a standard cloning vector and also to express the ACP gene in high efficiency expression vectors.

It is a further object of the invention to produce and recover ample quantities of synthetic ACP.

It is an object of one particular embodiment of the invention to provide, clone, and express in *E. coli* a synthetic gene encoding the entire amino acid sequence of spinach ACP-I.

It is another object of the invention to provide a prototype for a synthetic ACP gene designed for expression in plants and animals.

Other objects and advantages of this invention will become readily apparent from the ensuing description.

BRIEF DESCRIPTION OF THE DRAWINGS

FIG. 2 illustrates the nucleotide sequences and oligonucleotide fragments employed in the construction of the synthetic spinach ACP-I gene described in Example 1.

GLOSSARY

Figure 1:
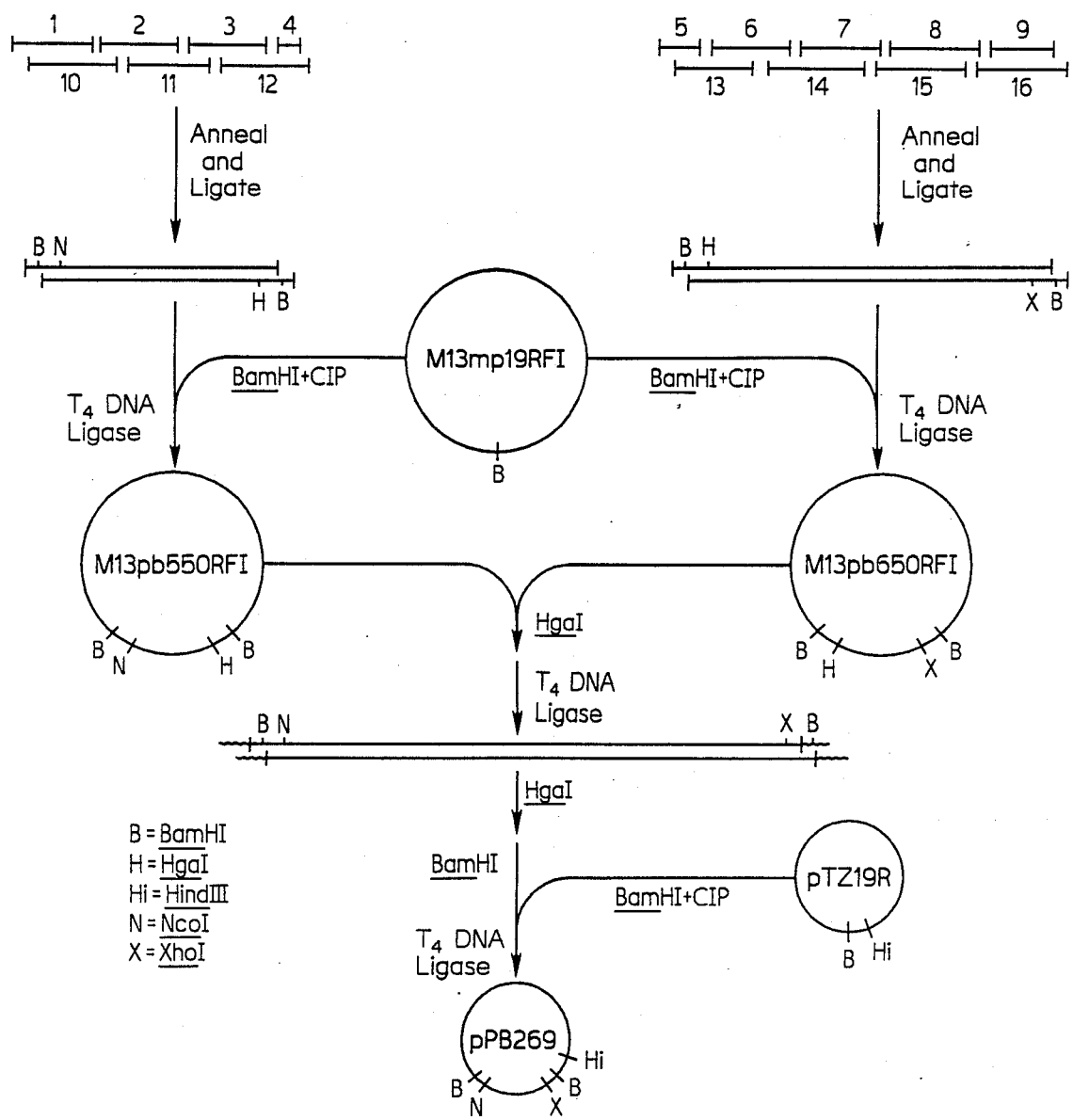
FIG. 1 is a flow diagram illustrating the strategy for constructing and cloning the synthetic spinach ACP-I gene described in Example 1.

For purposes of this invention, the following standard abbreviations and terms used herein have been defined below. Also included are a listing of restriction enzymes and an appendix of biological materials mentioned in the specification.

Abbreviations

ACP=acyl carrier protein
ACP-I=acyl carrier protein, isoform I
ACP-II=acyl carrier protein, isoform II
ATP=adenosine triphosphate
bp=base pairs
cDNA=single-stranded DNA complementary to a messenger RNA
DNA=deoxyribonucleic acid
MES=4-morpholineethanesulfonic acid
RNA=ribonucleic acid
trc=a high level promoter derived by fusion of the tryptophan (trp) and β-galactosidase promoter (lac)
YT=yeast extract+tryptone growth medium (8 g/l tryptone, 5 g/l yeast extract, 5 g/l NaCl)

Terms clone: in reference to DNA, the product or process of isolating a segment of DNA, linking it to a vector, and introducing it into a host for expression
expression: the transcription of a gene into messenger RNA (mRNA) and the subsequent translation of the mRNA into a protein coded by the gene
expression vector: a DNA sequence such as an amplicon, phage, or plasmid which is able to replicate in a host cell and express genes present in the DNA sequence
gene: a segment of DNA which encodes a specific protein or polypeptide, or RNA
hybridization: the pairing together or annealing of single-stranded regions of nucleic acids to form double-stranded molecules
linker: synthetic oligonucleotide containing a site for a restriction enzyme
phage: a bacteriophage; a virus which infects bacteria
plasmid: circular double-stranded DNA capable of autonomous replication within a bacterium
polylinker: array of restriction enzyme recognition sites (each of which is usually 4–8 bases long) linked together
probe: a labelled nucleic acid fragment which will hybridize with complementary nucleic acid sequences, and thereby be useful for detecting specific nucleic acid fragments
promoter: a recognition sequence for binding of RNA polymerase
subclone: in reference to DNA, the product or process of cloning a portion of an already cloned DNA segment
transform: to change in a heritable manner the characteristics of a host cell in response to DNA foreign to that cell
transgenic: relating to new genetic information becoming embedded into a germline
vector: a nucleic acid molecule such as a plasmid or phage and having a site for inserting a gene of interest for cloning, transfer, or expression

| Restriction Enzyme | Cleavage Site |
|---|---|
| BamHI | 5'... G ↓ GATCC ... 3' |
| HindIII | 5'... A ↓ AGCTT ... 3' |
| HgaI | 5'... GACGC(N)$_5$ ... 3' |
|  | 3'... CTGEG(N)$_{10}$ ... 5' |
| NcoI | 5'... C ↓ CATGg.3' |
| XhoI | 5'... C ↓ TCGAg.3' |

Appendix of Biological Materials
E. coli cells:      Source

| | |
|---|---|
| DH5 | BRL |
| DH5α | BRL |
| JM101 | Clontech |
| JM103 | J. Messing |
| JM109 | J. Messing |
| Enzymes: | |
| T$_4$ (polynucleotide kinase) | N.E. Biolabs or BRL |
| T$_4$ (DNA lignase of bacteriophage) | IBI |
| calf intestinal phosphatase | Boerhinger |
| Plasmids and Phage: | |
| M13mp19RFI (M13) | Pharmacia |
| pPB104 | NRRL B-18218 |
| pPB269 | NRRL B-18219 |
| pKK233-2 | J. Brosius |
| pTZ19R | Pharmacia |

DETAILED DESCRIPTION OF THE INVENTION

For purposes of the invention, the expression "synthetic ACP gene" and equivalent expressions are defined to mean any nonnaturally occurring nucleic acid sequence which encodes acyl carrier protein (ACP). As previously discussed, it is recognized that ACP may exist in more than one isoform in a given species, and that the ACP structure varies from species to species. In fact, it is generally known that variations may exist in the amino acid sequence of a protein without any significant effect on its functional characteristics. It is also recognized that the coding sequences and the general construction of the synthetic gene may be varied considerably without altering the amino acid sequence of the encoded protein. The expression "synthetic ACP gene" is intended to encompass all such variations in gene structure.

The expression "plant ACP" refers to any acyl carrier protein having the essential functional characteristics of naturally occurring ACP molecules found in plants. The expressions "procaryotic ACP," "yeast ACP," and "animal ACP" are similarly defined, as are these same expressions when used in conjunction with the term "gene."

The first step in constructing a gene for expressing ACP is to predetermine the amino acid sequence of the specific protein to be encoded. In modeling the protein after an authentic ACP, slight variations may be made in the amino acid sequence without consequential effect on its functionality. Thus, certain amino acid additions, deletions, or substitutions inadvertently introduced or expressly designed into the protein structure would be contemplated as being within the purview of this invention.

The next step in gene construction is to select an appropriate nucleic acid triplet (codon) for encoding each amino acid within the latitude allowed by the redundancy of the genetic code. In order to optimize the synthetic gene as a probe for the naturally occurring homologous gene and mRNA, the gene's codon usage is made to reflect that of sequenced genes for other proteins in homologous systems. Creation of a codon usage table such as that employed in the Example below is a logical approach to this exercise. Unusual or disruptive nucleotide sequences within a codon, or created by adjacent codons, should be avoided. Also to be avoided are direct and inverted repeat sequences which would have a tendency to create undesirable mismatches or secondary structure.

The gene per se will usually be a component of larger synthetic recombinant DNA molecule including other DNA sequences. For example, it would be desirable to flank the gene with restriction endonuclease recognition sites as known in the art and to incorporate the gene into vectors for promoting assembly and expression. Of particular interest as vectors are plasmids and phages which lend themselves to cloning, transfer, and expression of the synthetic gene. Other sequences such as promoters, enhancers, and the like may also be built into the constructions.

While various approaches to construction may be taken, it is preferred to synthesize the complementary strands of the gene from overlapping oligonucleotide fragments ranging in size from about 10–60 nucleotides each. The oligonucleotides may be synthesized using a DNA synthesizer as known in the art, and they are subsequently ligated and annealed together using conventional enzymes and methodology. Depending on the size of the gene, either the complete sequence or parts thereof can be constructed in this manner.

By incorporating the ligation products into a suitable cloning vector, the gene or gene parts can be multiplied and selected by established criteria. If clones of components of the gene are selected, a stategy similar to that employed for assembling the oligonucleotide fragments can be applied to assembling the whole gene.

To achieve expression, the gene is subcloned from the cloning vector into a suitable expression vector. Typically the expression vector will provide both a promoter and a ribosome binding site upstream from the insert site. A start codon must also be provided at an appropriate site in the construction. A preferred expression system for in vitro production of ACP is $E.$ $coli.$ Of course, appropriate design modifications can be made in the synthetic ACP gene to achieve in vivo expression in plant cells.

The full-length synthetic ACP genes contemplated by this invention have utility as sensitive DNA and RNA probes to the ACP gene. In addition, clones partial genes and oligonucleotides such as those used in constructing the ACP-I gene described in the Example, below, have utility as probes for specific portions of the ACP gene. The successful expression of a synthetic plant ACP gene in $E.$ $coli$ or other vector system enables isolation of large quantities of the synthetic protein. This is also a first step toward achieving expression of authentic ACP-I from transformed plant cells or transgenic plants.

The ensuing Example drawn to construction of a synthetic spinach ACP-I gene is intended to illustrate the contruction of similar genes within the compass of the invention. Modifications to the design of the gene and strategy for its assembly and cloning would be obvious to the skilled artisan.

EXAMPLE

Design of a Synthetic Gene for Spinach ACP-I

The design of the 268-base pair, synthetic ACP gene described below was guided by the following 82 amino acid sequence of spinach ACP-I reported in the literature by Kuo et al. I, supra.

$$H_2N-\overset{1}{Ala}-Lys-Lys-Glu-Thr-Ile-Asp-Lys-Val-$$

$$\overset{10}{Ser}-Asp-Ile-Val-Lys-Glu-Lys-Leu-Ala-Leu-$$

$$\overset{20}{Gly}-Ala-Asp-Val-Val-Val-Thr-Ala-Asp-Ser-$$

$$\overset{30}{Glu}-Phe-Ser-Lys-Leu-Gly-Ala-Asp-Ser-Leu-$$

$$\overset{40}{Asp}-Thr-Val-Glu-Ile-Val-Met-Asn-Leu-Glu-$$

$$\overset{50}{Glu}-Glu-Phe-Gly-Ile-Asn-Val-Asp-Glu-Asp-$$

$$\overset{60}{Lys}-Ala-Gln-Asp-Ile-Ser-Thr-Ile-Gln-Gln-$$

$$\overset{70}{Ala}-Ala-Asp-Val-Ile-Glu-Leu-Leu-Glu-$$

$$\overset{80}{Lys}-Lys-Ala-COOH$$

Amino acid residue 76 was not identified in the original protein sequencing. Glycine occurs in this position in $E.$ $coli$ ACP, and the plant and bacterial sequences are approximately 50% homologous in this region. In addition, amino acids analysis of spinach ACP-I suggested a glycine residue could have been missed in the sequencing. Therefore, we designed the gene based on a glycine at position 76.

A plant codon usage table (Table I) was constructed using 18 sequences from the "Genbank" data base. The 18 sequences represent 4,478 amino acids. Ten of the sequences are from seed proteins, and there are four sequences for ribulose bisphosphate carboxylase small subunit from different plants. The probability of the occurrence of the third nucleotide for degenerate codons and the optimum codon for arginine, serine, and leucine were calculated as in Lathe [J. Mol. Biol. 183: 1–12 (1985)]. The initial ACP synthetic gene sequence was generated using the most probable codons in cases of degeneracy. In subsequent analyses, the dinucleotide CG was removed wherever possible from the sequence, as this dinucleotide is rare in the structural genes of eucaryotes (Lathe, supra). Codon usage in the gene sequence was further modified to remove direct or inverted repeat sequences greater than eight bases in order to eliminate undesirable mismatches or secondary structure in the oligonucleotides.

TABLE I

| | | U | | | | | C | | | | | A | | | | | G | | | |
|---|---|---|---|---|---|---|---|---|---|---|---|---|---|---|---|---|---|---|---|---|
| | 1 | 2 | 3 | 4 | 5 | 1 | 2 | 3 | 4 | 5 | 1 | 2 | 3 | 4 | 5 | 1 | 2 | 3 | 4 | 5 |
| U | 74 | 0.35 | 0.78 | Phe | U | 78 | 0.22 | 0.57 | Ser | U | 53 | 0.38 | 0.79 | Tyr | U | 10 | 0.19 | 0.78 | Cys | U |
| | 139 | 0.65 | 0.88 | Phe | C | 84 | 0.24 | 0.60 | Ser | C | 87 | 0.62 | 0.87 | Tyr | C | 42 | 0.81 | 0.94 | Cys | C |
| | 30 | 0.07 | 0.49 | Thr | A | 60 | 0.17 | 0.51 | Ser | A | | | | E1 | A | | | | E3 | A |
| | 94 | 0.22 | 0.55 | Thr | G | 22 | 0.06 | 0.47 | Ser | G | | | | E2 | G | 58 | 1.0 | 1.0 | Trp | G |
| C | 96 | 0.22 | 0.63 | Thr | U | 63 | 0.26 | 0.75 | Pro | U | 35 | 0.44 | 0.81 | His | U | 36 | 0.20 | 0.55 | Arg | U |
| | 93 | 0.22 | 0.63 | Thr | C | 55 | 0.23 | 0.74 | Pro | C | 44 | 0.56 | 0.85 | His | C | 31 | 0.17 | 0.54 | Arg | C |

TABLE I-continued

Plant Codon Usage

| | 1 | 2 | 3 | 4 | 5 | 1 | 2 | 3 | 4 | 5 | 1 | 2 | 3 | 4 | 5 | 1 | 2 | 3 | 4 | 5 |
|---|---|---|---|---|---|---|---|---|---|---|---|---|---|---|---|---|---|---|---|---|
|   |   |   |   |   |   |   |   | U |   |   |   |   | C |   |   |   |   | A |   |   |   |   | G |   |
|   | 59 | 0.14 | 0.63 | Thr | A | 97 | 0.40 | 0.80 | Pro | A | 200 | 0.64 | 0.88 | Gln | A | 12 | 0.06 | 0.59 | Arg | A |
|   | 60 | 0.14 | 0.67 | Thr | G | 27 | 0.11 | 0.70 | Pro | G | 113 | 0.36 | 0.78 | Gln | G | 10 | 0.05 | 0.58 | Arg | G |
| A | 83 | 0.34 | 0.78 | Ile | U | 73 | 0.32 | 0.77 | Thr | U | 77 | 0.33 | 0.78 | Ash | U | 39 | 0.11 | 0.31 | Ser | U |
|   | 120 | 0.49 | 0.83 | Ile | C | 99 | 0.43 | 0.81 | Thr | C | 153 | 0.67 | 0.89 | Ash | C | 71 | 0.20 | 0.35 | Ser | C |
|   | 40 | 0.16 | 0.72 | Ile | A | 38 | 0.17 | 0.72 | Thr | A | 88 | 0.38 | 0.79 | Lys | A | 50 | 0.27 | 0.62 | Arg | A |
|   | 88 | 1.0 | 1.0 | Met | G | 18 | 0.08 | 0.69 | Thr | G | 143 | 0.62 | 0.87 | Lys | G | 43 | 0.24 | 0.60 | Arg | G |
| G | 84 | 0.27 | 0.76 | Val | U | 119 | 0.32 | 0.77 | Ala | U | 93 | 0.47 | 0.81 | Asp | U | 74 | 0.27 | 0.75 | Gly | U |
|   | 65 | 0.21 | 0.73 | Val | C | 123 | 0.34 | 0.78 | Ala | C | 106 | 0.53 | 0.84 | Asp | C | 94 | 0.34 | 0.78 | Gly | C |
|   | 42 | 0.14 | 0.71 | Val | A | 83 | 0.23 | 0.74 | Ala | A | 103 | 0.43 | 0.81 | Glu | A | 60 | 0.22 | 0.74 | Gly | A |
|   | 117 | 0.38 | 0.79 | Val | G | 41 | 0.11 | 0.70 | Ala | G | 137 | 0.57 | 0.86 | Glu | G | 44 | 0.16 | 0.72 | Gly | G |

1. Number of times a particular codon was used out of 4,470 amino acids screened.
2. Probability of usage of particular codon.
3. Certainty factor or overall homology for codon [see Table 5, Lathe, J. Mol. Biol. 183: 1-12 (1985)].
4. Amino acid, three letter code.
5. Third nucleotide in codon.

Sequences used to determine codon usage: *Hordeum vulgare* α-amylase (cDNA); *Hordeum vulgare* B1 hordein (cDNA); *Lemna gibba* ribulose bisphosphate carboxylase small subunit (cDNA); *Zea mays* 22 Kd. zein protein (cDNA); *Zea mays* alcohol dehydrogenase ADH1 (cDNA); *Zea mays* zein clone A30 (cDNA); *Nicotiana sylvestris* ribulose bisphosphate carboxylase small subunit (cDNA); *Petroselinum hortense* chalcone synthase (cDNA); *Pisum sativum* legumin subunit pair precursor (cDNA); *Pisum sativum* lectin (alpha and beta subunits) (cDNA); *Pisum sativum* ribulose biphosphate carboxylase small subunit (cDNA); *Pisum sativum* vicilin (cDNA) (two separate clones); *Phaseolus vulglaris* lectin (cDNA); *Glycine max* 7S seed storage protein α + α¹ (cDNA); *Glycine max* actin gene; *Glycine max* lectin gene; *Glycine max* ribulose bisphosphate carboxylase small subunit gene (cDNA); *Triticum aestivum* α-gliadin (cDNA).

The overall strategy for construction and cloning of the synthetic gene is outlined in FIG. 1. Numbers 1–16 refer to the oligonucleotides depicted in FIG. 2.

As shown in FIG. 2, two gene fragments, one encoding the amino-terminal portion (A) and the other the carboxy-terminal portion (B) of the protein, were separately assembled from 16 synthetic oligonucleotides. The numbers correspond to the amino acids of the mature protein. The approach of assembling the oligonucleotide into two gene fragments facilitated cloning.

BamHI sites were positioned at the 3' end of the amino-terminal segment and the 5' of the carboxy-terminal segment as shown in FIG. 1. These sites were designed to facilitate insertion of the respective segments into the cloning plasmids. Because HgaI generates 5' overhangs of five bases outside of its recognition site, HgaI sites were oriented in the segments in a manner such that digestion with the enzyme removed the HgaI and the adjacent BamHI sites from the rest of the construction. This procedure allowed for the generation of unique cohesive ends between the two half-gene clones, which when annealed and ligated, resulted in a full-length ACP coding sequence, without the flanking sites at the junction.

Oligonucleotide Synthesis

The oligonucleotide were synthesized on an Applied Biosystems 381 A DNA synthesizer, using diisopropylmethyl phosphoramidites for the fragments of one strand of each part, and diisopropyl cyanoethylphosphoramidites for the fragments of the other part. The 16 fragements were deblocked and cleared from the solid support by NH₄OH treatment. After desalting on Sephadex-G50, the fragments were purified by gel electrophoresis in 8M-urea/12% acrylamide gels.

Partial Gene Constructions

Following oligonucleotide purification, all fragments except those with a 5' BamHI site (the 5' ends of the construction) were individually phosphorylated with T₄ polynucleotide kinase. Fragments were annealed in separate reactions containing two or three complementary oligonucleotides.

Oligonucleotides 1 and 10; 2, 3, and 11; 4 and 12 were annealed in separate tubes and then sequentially ligated, yielding the coding sequence for the amino-terminal portion of ACP-I. Similarly, oligonucleotides 5 and 13; 6, 7, and 14; 8 and 15; 9 and 16 were annealed and ligated to yield the coding sequence for the carboxy-terminal portion of the protein. In each case, a small (1–3%) but easily detected portion of the ligation products was found to be of the appropriate size (124 bp and 170 bp) for the desired construction. In a typical reaction the fragments were present at 12 μM in 10 mM Tris-Cl (pH 7.4), 10 mM NaCl, and 10 mM MgCl₂. After briefly heating to 80° C., the reactions were allowed to cool slowly to room temperature. The annealing reactions were then mixed sequentially and ligated to 14° C. with 1 unit/ml T₄ DNA ligase, in the presence of 667 μM ATP and 4.4 mM dithiothreitol. Each ligation was allowed to proceed 30 min. before the addition of the next annealed set of oligonucleotides. Additional ligase, ATP, and dithiothreitol were added after each addition to maintain the appropriate concentrations. Thirty minutes after the final addition, the reaction was stopped by heating to 70° C. for 5 min.

Cloning of Synthetic DNA

The synthetic DNA ligation products were ethanol precipitated and phosphorylated with T₄ polynucleotide kinase. The phosphorylated synthetic DNA (0.2 pmol) was then mixed with (0.02 pmol) BamHI digested phage M13mp19RFI DNA which had been dephosphorylated with calf intestinal phosphatase to prevent self-ligation. The reactions were carried out at 4° C. for 12 hours, with T₄ DNA ligase present at 0.5 unit/ml, followed by an hour at 4° C. with 7.5 units/ml.

The ligation products were then used to transform competent *E. coli* cells, strain DH5. The transformed cells were plated in soft agar containing *E. coli* cells, strain JM109, isopropyl-β-D-thiogalactopyranoside, and 5-bromo-4-chloro-3-indoyl-β-D-galactoside onto B-agar plates. White plaques were picked, and recombinant phage were slot blot screened by preparing singlestranded DNA using the method of Sanger et al. [J. Mol. Biol. 143: 161–178 (1980)], binding the DNA to nitrocellulose, and hybridizing with ³²P-labelled oligonucleotide probes. Oligonucleotides were labelled according to Maxam and Gilbert [Proc. Natl. Acad. Sci. 74: 560–564 (1977)], using [γ³²P]ATP (Amersham) and T4 polynucleotide kinase. For both half-gene constructions, a significant number of clones showed positive signals; 19 of 23 analyzed for the first half and 24 of 57 analyzed for the second half. The desired construct should have been the only product that was completely double-stranded, with two BamHI cohesive ends. Thus, ligation to the vector and subsequent transformation of E. coli provided a strong selection for the correct construct. DNA sequencing confirmed that a number of these positive clones did contain the exact sequences which had been synthesized. Some positively hybridizing clones contained deletions or base substitutions.

Construction and Cloning of a Full-Length ACP-I Sequence

M13 clones for both the 3' and 5' ends of the ACP-I gene were propagated on E. coli JM103, and replicative form DNA was prepared from each according to Zoller et al. [DNA 3: 479–488 (1984)]. Equimolar amounts of each replicative form were mixed together and digested to completion with HgaI to eliminate the extraneous bases in the shaded region of FIG. 2.

The digestion products comprising multiple fragments of DNA were adjusted to 2.5M NH$_4$OAc and ethanol precipitated. The DNA was resuspended at a final concentration of 0.5 mg/ml and the fragments ligated with 12.5 units/ml ligase at 16° C. for 1 hour. The reaction was then heated to 70° C. for 5 min. to prevent any further reaction. The DNA was again subjected to HgaI digestion followed by BamHI digestion to cut any ligation products which were the result of reformation of the original constructs. Finally, the reaction was extracted with phenol and chloroform, the aqueous phase adjusted to 0.3M NaOAc and 0.01M MgCl$_2$, and the DNA precipitated with ethanol. The DNA obtained from this procedure was mixed with T$_4$ DNA ligase and ligated to pTZ19R DNA, which had been previously digested with BamHI and dephosphorylated with calf intestinal phosphatase. Conditions were as described for cloning into M13, except that 68 ng of pTZ19R and 115 ng of the precipitated DNA were used in a 10-μl reaction.

The ligation products were used to transform competent E. coli cells, strain DH5α. Transformants were selected on 5-bromo-4-chloro-3-indolyl-β-D-galactoside+ampicillin plates. White colonies were picked and their plasmid DNA screened on slot blots. Fifty white colonies were analyzed and eight showed hybridization with probes for both halves of the gene. These eight plasmids were digested with BamHI and the digestion products analyzed on agarose gels. All eight plasmids contained an appropriately sized BamHI insert (268 bp). Two also contained a 170-bp insert, and two apparently contained a 37-bp fragment very likely corresponding to the ligation of the Hga-Bam fragments removed from the ends of each half-gene. Clones containing only the 268-bp insert were sequenced, confirming the proper assembly of the full ACP-I gene as shown in FIG. 2. The plasmid carried by one such clone was designated pPB269. This plasmid has been cloned in E. coli DH5α, and as such has been deposited under the Budapest Treaty with the Agricultural Research Service in Peoria, IL, and has been assigned NRRL Accession No. B-18219. Restriction analysis indicated that the ACP-I gene was oriented within the polylinker as indicated in FIG. 1.

Expression of Spinach ACP-I gene in E. coli

In order to express the synthetic spinach ACP-I gene in E. coli, it was subcloned from pPB269 into the expression vector pKK233-2 [Amann et al., Gene 40: 183–190 (1985)]. This vector provides both a trc promoter and a ribosome binding site upstream from the insert site. In addition, the start codon is optimally spaced relative to the ribosome binding site, and proper positioning of inserts is guaranteed by the presence of an NcoI recognition site at this start codon. An NcoI site at the start codon was designed into the synthetic ACP-I gene to facilitate cloning into this and other similar expression vectors.

The NcoI/HindIII fragment containing the ACP-I gene was ligated into the NcoI and HindIII sites of pKK233-2 and introduced into E. coli cells, strain JM101.

Immunoscreening of Spinach ACP Expressing Colonies

Colonies of recombinant clones were screened for the expression of the spinach ACP-I gene with antibody following their transfer to nitrocellulose and lysis by the method of Helfman et al. [Proc. Natl. Acad. Sci. 80: 31–35 (1983)]. Bound ACP-I antibody (rabbit) was visualized with an alkaline phosphatase linked antirabbit antibody system from Promega Biotec. Controls indicated that E. coli ACP did not give a strong positive signal with the antibody to spinach ACP-I that had been blocked with E. coli lysates. Plasmid DNA was prepared from colonies showing a positive signal. These plasmids were digested with NcoI and HindIII and screened for insert size. Several plasmids with the appropriately sized insert were detected. One, pPB104, has been cloned in E. coli JM109, and as such has been deposited under the Budapest Treaty with the Agricultural Research Service in Peoria, IL, and has been assigned NRRL Accession No. B-18218.

Western Blot Analysis of ACP-I Expression in E. coli

Western blot analysis of spinach ACP-I expression in E. coli JM101 cells containing no plasmid, pKK233-2, or pPB104 were grown to an OD$^{550}$ of 0.6 in 3 ml of LB medium. The cells were centrifuged and the pellets resuspended in 5 ml of YT medium. One-half of each plasmid-containing culture was then induced by the addition of isopropyl-β-D-thiogalactoside to 1 mM. All cultures were grown for an additional 3 hours to an OD$^{550}$ of 2.3. One milliliter of each culture was centrifuged and the cell pellets boiled for 5 min. in 800 μl of sample buffer. Extracts (2 μl) of JM101, JM101 carrying uninduced pKK233-2, JM101 carrying induced pKK233-2, 10 ng spinach ACP-I, JM101 carrying uninduced pPB104, JM101 carrying induced pPB104, and 20 ng E. coli ACP were applied separately to 15% NaDodSO$_4$ polyacrylamide gels.

Western blots of these gels were probed with antibody (rabbit) to ACP-I. Proteins binding the anti ACP-I were detected with alkaline phosphatase-linked, antirabbit antibody. The results indicate that E. coli ACP was barely detectable under the conditions employed (antibody blocked with E. coli extracts). Furthermore, crossreacting material was not found in extracts from JM101 cells containing no plasmid or containing pKK233-2 without an insert. However, cells containing pPB104 showed a strongly crossreacting band of protein, with electrophoretic mobility nearly identical to purified spinach ACP-I. This protein was induced by isopropyl-β-D-thiogalactopyranoside approximately fourfold, but it was also present at easily detectable levels in uninduced cultures.

Characterization of the Synthetic Gene Product

A 4-liter culture of JM101 cells containing pPB104 was grown in YT medium to an $OD^{550}$ of approximately 10. The harvested cell pellet was extracted by homogenization in 10 vol 0.1M Tris, 0.1M glycine, 25 mM EDTA (pH 8.0). Lysozyme (10 μg/g cell pellet) was added, and the suspension was stirred for 2 hours before passage through a French pressure cell. Ater centrifugation at 4,000 g for 30 min., the supernatant was adjusted to 65% ammonium sulfate, centrifuged as before, and the supernatant adjusted to 2.5% TCA. After standing 1.5 hours at 4° C., the acid pellet was collected by centrifugation, redissolved in 10 ml 10 mM MES (pH 6.1) and dialyzed against 200 vol of 10 mM MES, 0.5 mM dithiothreitol (pH 6.1) overnight. The dialysate was applied to a 2.5×5.0 cm. DE53 column (Whatman) and eluted with a 150-ml linear salt gradient (0.0 fo 0.5M LiCl) in 10 mM MES, 2 mM dithiothreitol (pH 6.1). Fractions were assayed for holo ACP using *E. coli* acyl-ACP synthetase and for spinach ACP-I using a radioimmunoassay [Kuo et al. III, Anal. Biochem. 136: 479-502 (1984)]. In a competitive binding radioimmunoassay, which is very sensitive to differences in ACP structures [Ohlrogge et al. II and Kuo et al. III supra], the spinach ACP-I produced in *E. coli* competed completely with ACP-I purified from spinach leaves. From radioimmunoassay of cell extracts, we estimate that approximately 6 mg of ACP-I protein is produced per liter of induced culture or roughly 1% of total cell protein.

The *E. coli* cells producing spinach ACP-I are able to attach the phosphopantetheine prosthetic group in vivo to the plant protein to form holo ACP-I. This is demonstrated by the ability of the partially purified synthetic gene product to be acylated by *E. coli* acyl-ACP synthetase. Extracts of *E. coli* cells expressing the synthetic gene were fractionated by ion exchange chromatography on DEAE-cellulose. During elution with a LiCl gradient, spinach ACP-I elutes before *E. coli* ACP. Two peaks of activity, measured enzymatically, were eluted from the column but only the first ACP peak was active in a radioimmunoassay for spinach ACP-I. Thus, the first ACP peak is enzymatically active spinach ACP-I produced from the synthetic gene, and the second peak is *E. coli* ACP. These identifications were confirmed by $NaDodSo_4$/PAGE analysis of the separate peaks. The quantity of holo-spinach ACP-I measured by its acylation with [$^3$H]palmitate is similar to the quantity determined by radioimmunoassay. Because acylation by palmitate requires holo ACP, whereas the radioimmunoassay responds to both holo and apo ACP, it appears that most of the spinach ACP-I produced in *E. coli* contains the phosphopantetheine prosthetic group.

It is understood that the foregoing detailed description is given merely by way of illustration and that modification and variations may be made therein without departing from the spirit and scope of the invention.

We claim:

1. A recombinant DNA which encodes spinach acyl carrier protein-I-Gly$^{76}$.

2. A recombinant DNA construct comprising a DNA which encodes spinach acyl carrier protein-I-Gly$^{76}$.

3. The construct of claim 2 wherein said construct is a plasmid.

4. A construct as described in claim 2 wherein said construct is a cloning vector.

5. A construct as described in claim 2 wherein said construct is an expression vector.

6. A construct as described in claim 2 wherein said construct is a plasmid for expressing said gene in *E. coli*.

7. A phage comprising the recombinant DNA construct of claim 2.

8. A method of producing enzymatically active spinach acyl carrier protein-I-Gly$^{76}$ comprising:
   a. transforming cells for expressing said protein with an expression vector carrying a recombinant DNA which encodes said protein;
   b. culturing said cells under conditions wherein said protein is expressed.

9. The method of claim 8 wherein said cells are *E. coli* cells.

* * * * *